(12) United States Patent
Gedon et al.

(10) Patent No.: US 6,998,499 B2
(45) Date of Patent: Feb. 14, 2006

(54) PROCESS FOR THE PREPARATION OF SECONDARY AND TERTIARY AMINO-FUNCTIONAL SILANES, IMINOORGANOSILANES AND/OR IMIDOORGANOSILANES

(75) Inventors: Steven C. Gedon, Williamstown, WV (US); Andrea Trotto, Termoli (IT)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/458,036

(22) Filed: Jun. 10, 2003

(65) Prior Publication Data

US 2003/0220513 A1    Nov. 27, 2003

Related U.S. Application Data

(62) Division of application No. 09/990,959, filed on Nov. 16, 2001, now Pat. No. 6,586,612.

(51) Int. Cl.
*C07F 7/02*    (2006.01)

(52) U.S. Cl. .................................. 556/413; 556/411
(58) Field of Classification Search ............ 556/413, 556/441, 406, 418, 419
See application file for complete search history.

(56) References Cited

U.S. PATENT DOCUMENTS

| | | | |
|---|---|---|---|
| 2,513,996 A | 4/1950 | Haury | |
| 2,582,128 A | 1/1952 | Hurwitz | |
| 2,942,019 A | * | 6/1960 | Pike et al. .................. 556/413 |
| 4,045,486 A | 8/1977 | Krall et al. | |
| 4,378,250 A | 3/1983 | Treadway et al. | |
| 5,866,262 A | 2/1999 | Galic et al. | |
| 6,072,085 A | 6/2000 | Verdaguer et al. | |
| 6,191,286 B1 | 2/2001 | Gunther et al. | |

OTHER PUBLICATIONS

CA:123:144261 abs of JP 06228165 Aug. 1994.*
CA:124:146469 abs of JP 07247294 Sep. 1995.*
CA:111:215542 abs of DD 266363 Mar. 1989.*
CA:93:205753 abs of JP 55075469 Jun. 1980.*
CA: 707:156507 abs of JP62083430 Apr. 1987.*
CA:78:111411 abs of Doklady Akademii Nauk SSSR by Nametkin et al 207(6) pp 1358-61 1972.*
CA:79:42602 abs of Izvestiya Akademii Nauk SSSR, Seriya Khimicheskaya by Nametkin et al (4) pp 865-70 1973.*
CA:97:6375 abs of Zhurnal Obshchei Khimii by Perchenko et al 52(2) pp 362-80 1982.*
CA:102:24702 abs of Zhurnal Obshchei Khimii by Chernyshev et al 54 (9) pp 2031-4 1984.*
CA:110:213072 abs of CS 245443 Oct. 1986.*
CA:100:192926 abs of DE 3220865 Dec. 1983.*
*Silica-Supported Imines as Mild, Efficient Base Catalysts* by Katherine A. Utting and Duncan J. Macquarrie, appearing in New Journal of Chemistry at pp. 591-595 (2000) No. 24.
*A Convenient Synthesis of Amines* by Kumar et al., appearing in Indian Journal of Heterocyclic Chemistry. vol. 10, Jul.-Sep. (2000) at pp. 79-80.

* cited by examiner

*Primary Examiner*—Johann Richter
*Assistant Examiner*—Chukwuma Nwaonicha
(74) *Attorney, Agent, or Firm*—Dominick G. Vicari

(57) ABSTRACT

Iminoorganosilanes may be prepared by reacting aminoorganosilanes with organoimines by an amine exchange reaction. The resultant iminoorganosilanes can then be catalytically reduced to produce secondary and tertiary amino silanes. Imidoorganosilanes can be prepared by a similar amine reaction between aminoorganosilanes and organoimides. The imidoorganosilanes can also be reacted to produce tertiary amines. Water-sensitive silane reactants may be employed to yield water-sensitive imino, imido, or amino silane products.

12 Claims, No Drawings

PROCESS FOR THE PREPARATION OF SECONDARY AND TERTIARY AMINO-FUNCTIONAL SILANES, IMINOORGANOSILANES AND/OR IMIDOORGANOSILANES

This application is a divisional of U.S. patent application Ser. No. 09/990,959, filed Nov. 16, 2001 now U.S. Pat. No. 6,586,612.

FIELD OF THE INVENTION

The present invention relates to an improved process of producing secondary and tertiary amino-functional silanes, and to the novel silyl imines, silyl imides, and secondary and tertiary amino-functional silanes produced therefrom.

BACKGROUND OF THE INVENTION

Amino silanes are commonly used as adhesion promoters in adhesives and sealants, and as coupling agents in compositions used in the plastics and glass-fibers industries and in foundries, in fabric treatment compositions, and in personal care products.

In particular, secondary and tertiary amino functionalized silanes are useful as coupling agents in the fiberglass and automotive glass industries. Currently the best technology for producing functionalized amino silanes is either through hydrosilation of a functionalized allyl amine, through reductive amination of a primary amino silane, or by nucleophilic substitution of gamma-chloropropyltrialkoxysilane. Unfortunately, functionalized allyl amines are not readily available, and are often quite expensive when they are available. Reductive aminations, on the other hand, are limited to symmetrical secondary amines, and often occur in such low yields that they are cost prohibitive, while nucleophilic substitution generates one equivalent of hydrochloride salt that must be recycled or disposed of.

Primary amines are one of the more reactive functional groups in organic chemistry and are known to react rapidly with a variety of carbonyl containing compounds. In the case of aldehydes and ketones, nucleophilic addition and dehydration results in an analogous imine structure that forms almost quantitatively at room temperature. Subsequent reduction of the imine functionality has been shown to provide an economical route to secondary amines. While the application of this methodology to amino silanes has already been reported in the patent literature, the direct reaction of silanes with aldehydes or ketones inevitably leads to the formation of siloxanes and lower yields.

SUMMARY OF THE INVENTION

The present invention overcomes the aforementioned problems by performing a water-producing condensation reaction between a carbonyl compound and a water-insensitive carrier amine, for instance butyl amine or aniline, to give an imine as the first intermediate adduct product; after removing water from the product and drying by conventional means, the carrier amine is then regenerated and recovered in an exchange reaction with a water sensitive aminoorganosilane to produce a second silyl imine intermediate adduct which is further reduced to either a secondary or tertiary amine depending on the nature of the aminoorganosilane.

The starting carbonyl compound may be a ketone, aldehyde, carboxylic acid or anhydride. In the case where the carbonyl compound is an aldehyde or ketone, the first and second intermediate adduct products are imines (i.e. aldimines and ketimines, respectively). Compounds which exist as aldehyde and ketone equivalents, e.g. ketals and acetals, may also be used to produce imine intermediates. In the case where the carbonyl compound is an anhydride or carboxylic acid, the resulting intermediate compounds are amides.

The use of secondary amino silanes as adhesion promoters is well known in urethanes and glass sizing agents. The conversion of silyl imines, produced by the process described above, to secondary amine can be accomplished under moderate hydrogen pressure and in the presence of a precious metal catalyst, i.e. Pd, Pt, Rh-containing catalysts, and the like. Other reduction methods for conversion of imines to secondary amines are also applicable and have been described in the prior art and are equally as applicable.

Using the method of the present invention, a whole new class of novel secondary amines, not possible using other methods, becomes available. In the case where an imine or imide of a volatilizable amine is already available, the first step of the process may be eliminated.

The second intermediate compounds, i.e. ketimino, aldimino and imido silanes, produced by the process of the invention have utility in their own right, as adhesion promoters, crosslinkers, as components of silicate clearcoats and the like. EP 976771, incorporated by reference herein in its entirety, describes a curable resin composition containing a curable resin and a ketimine structure-bearing organosilicon compound that is useful as an adhesive. With respect to such compounds, therefore the final reduction step in the process described above may be eliminated.

The present invention herein also relates to the novel secondary and to novel second intermediate compounds, i.e. ketimino, aldimino and imido silanes, formed by the processes as described above.

DETAILED DESCRIPTIONS OF THE PREFERRED EMBODIMENTS

The present invention provides a process whereby novel and valuable silyl imines or silyl imides having hydrolyzable groups bound to silicon can be produced and isolated. Silyl imines and imides produced by this method can be obtained in high yield and substantially siloxane-free. More particularly, the process of the invention provides product yields typically exceeding 90% and containing less than about 2 weight percent siloxanes. Moreover, subsequent reduction of the aforementioned imines provides a novel route to secondary and tertiary amines.

The steps of the invention are described in sequence, although as noted, the formation of the first intermediate may be eliminated if that product is available and the reduction to amine may be eliminated if the compound described herein as the second intermediate is the desired end product.

The process steps of the present invention can be practiced using either a batch mode process, or using a continuous process.

Step 1—Formation of First Intermediate Imine or Imide

The first step in the process of the invention involves a condensation reaction which forms an imine or imide from a water insensitive volatilizable primary amine (a "carrier" amine) and a carbonyl compound. The imine forming condensation reaction may be represented by the following general reaction (I):

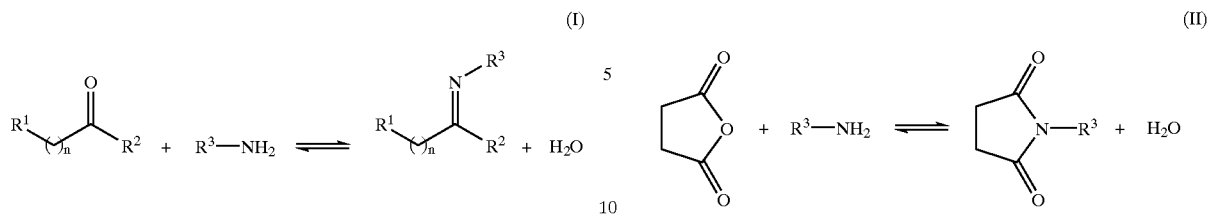

In formula (I), $R^1$ is a hydrocarbon group, suitably one having from 1 to 30 carbon atoms, although in principle even larger hydrocarbon groups may be employed as $R^1$ groups, and may be an alkyl, aryl, alkaryl, aralkyl or alkarylalkyl group. Preferably, $R^1$ has from 1 to 20 carbon atoms. $R^1$ may also be an alkenyl or alkynyl group, although in such cases the final reduction step will likely hydrogenate some or all of the sites of aliphatic carbon-carbon unsaturation. $R^2$ is hydrogen or a hydrocarbon group having from 1 to 20 carbon atoms, more preferably from 1 to 4 carbon atoms, and may be suitably an alkyl, aryl, alkaryl, aralkyl or alkarylalkyl group, or $R^1$ and $R^2$ together form a cyclic hydrocarbon group containing up to 8 carbon atoms. $R^3$ is a hydrogen or a hydrocarbon group having from 1 to 10 carbon atoms, more preferably from 3 to 8 carbon atoms, and may be an alkyl, aryl, alkaryl, aralkyl or alkarylalkyl group, and n is 0 to 20, preferably 1 to 3.

In one specific embodiment of the reaction depicted above, $R^1$ is benzyl, $R^2$ is hydrogen and $R^3$ is phenyl.

The primary carrier amines, $R^3NH_2$, useful herein include but are not limited to, allyl amine, ammonia, aniline, butyl amine, ethyl amine, isopropyl amine, tert-octyl amine, and so forth. Preferred amines are relatively low boiling, or are amines which will form a readily volatilizable azeotrope with a non-aqueous solvent such as toluene. Butylamine, which has a boiling point of about 76° C., is an example of a preferred relatively low boiling amine. Aniline, which can be azeotropically distilled with toluene, is an example of an amine which is readily volatilizable with a non-aqueous solvent.

The condensation reaction (I) above may also be implemented starting with a compound which exists in equilibrium with an aldehyde or ketone, in particular an acetal, ketal, or an aldehyde-ammonia trimer.

Useful aldehydes include, but are not limited to, formaldehyde, acetaldehyde, butyraldehyde, hexanal, 2-ethyl hexanal, benzaldehyde, 1,4-terephthaldicarboxyaldehyde, glutaric dialdehyde, furfuraldehyde, and so forth. The aldehydes useful in carrying out the invention include difunctional aldehydes, such as difunctional terephthaldehyde, which ultimately result in production of difunctional amino silanes.

Useful ketones include, but are not limited to, cyclohexanone, acetone, butanone, acetophenone, and so forth.

Useful aldehyde-ammonia trimers include, but are not limited to, 2,4,6-trimethyl-1,3,5-hexahydrotriazine.

The carrier amine $R^3NH_2$ may also be reacted with an anhydride or carboxylic acid. In this instance, a silyl imide intermediate is formed in the subsequent Step 2, described hereinbelow, rather than a silyl imine intermediate. The reaction is illustrated by the condensation of an amine with succinic anhydride as depicted in equation (II):

In equation (II), $R^3$ is as previously defined.

The formation of succinimides is described in U.S. Pat. No. 5,145,984 and in U.S. Pat. No. 5,286,873, both of which are incorporated by reference herein in their entirety. Similarly, bisimide formation is described in EP 342 823, incorporated by reference herein in its entirety.

Again, as in the case of imine formation, when the amine reacts with the anhydride at room temperature, water is liberated. In the case where a di-carboxylic acid is used two moles acid are consumed in the reaction and two moles of water will be produced.

In the reaction of equation (II) any carboxylic acid or anhydride thereof may be used. Carboxylic acids having from 1 to 22 carbon atoms and their anhydrides are preferred.

Useful anhydrides include, but are not limited to, succinic anhydride, maleic anhydride, glutaric anhydride, acetic anhydride, propionic anhydride, and so forth.

Useful carboxylic acids include, but are not limited to, succinic acid, maleic acid, glutaric acid, acetic acid, propionic acid, butyric acid, and various fatty acids such as lauric, myristic, palmitic, steric and so forth.

In a specific embodiment of the present invention, the resultant imine is N-benzylidene aniline where $R^1$ is phenyl, n is 1, $R^2$ is hydrogen, and $R^3$ is phenyl.

In another embodiment of the present invention, the resultant imine is N-cyclohexylidene butylamine where $R^1$ and $R^2$ are cyclohexyl, n is 0, and $R^3$ is n-butyl.

The bulk water produced in the condensation reaction of an aldehyde or ketone with a primary amine can be removed by conventional means, such as phase separation with a separatory funnel or by azeoptropic distillation. Optionally, residual water can be removed using an inorganic dessicant such as sodium sulfate, magnesium sulfate, molecular sieves, and the like.

Step 2—Formation of Second Intermediate by Exchange with Silylalkylamine

The imine, or imide product of the first step, after drying, is then subjected to an exchange reaction with a primary aminoalkylsilane under anhydrous conditions to form a corresponding iminoalkylsilane or imidoalkylsilane. The carrier amine, $R^3NH_2$, used in step 1 is regenerated in this step and can be reused.

The reaction of the second step is illustrated for imines by the following equation (III):

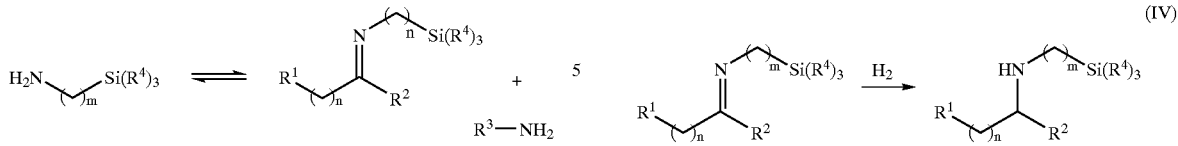

In equation (III), $R^1$, $R^2$, $R^3$ and n are as previously defined, each $R^4$ is independently hydrogen, a hydrocarbon group having from 1 to 8 carbon atoms, an alkoxy, or an acyloxy groups, and m is 2–20, preferably 3–5. Preferred $R^4$ groups include hydrocarbon groups containing from 1 to 8 carbon atoms, more preferably from 1 to 3 carbon atoms. Some specific examples of $R^4$ include, but are not limited to, methyl, ethyl, butyl, propyl, phenyl, benzyl, methoxy, ethoxy, butoxy, propoxy, and acetoxy.

Since the invention is particularly advantageous in the manufacture of water sensitive amino silanes it is preferred that at least one of the $R^4$ groups, more preferably 2 or 3 of the $R^4$ groups, are hydrolyzable alkoxy groups, for instance methoxy, ethoxy or isopropoxy, or acyloxy groups, for instance acetoxy. However, it should be understood that the invention can also be used to produce aminoalkylsilanes which are not water sensitive, such as where the $R^4$ groups are all methyl groups.

Under similar conditions a primary aminoalkylsilane $H_2N(CH_2)_mSi(R^4)_3$, will also exchange with an imide produced in the first step to give the corresponding imidoalkylsilane and regenerated carrier amine $R^3NH_2$.

Exemplary silanes which may be employed in this exchange reaction include gamma-amino propyl triethoxy silane sold under the tradename as Silquest A-1100 silane or ganuna-amino propyl trimethoxy silane, sold under the tradename as Silquest A-1110 silane, both available from Crompton Corporation (Middlebury, Conn.).

The regenerated carrier amine $R^3NH_2$ is suitably removed under reduced pressure and recycled.

The iminoalkylsilanes and imidoalkylsilanes having at least one hydrolyzable alkoxy or acetoxy group thereon which are produced in this step are novel compounds which are useful as adhesion promoters, fiber sizing agents and the like. Consequently, if desired, the products of this exchange step may be isolated and used without being subjected to the third, reduction, step described below.

It should also be recognized that in the case where a suitable imide or imine is available from another source the first step in the process may be eliminated and the exchange reaction of this step may be performed directly on such an imide or imine. N-methyl succinimide and N-methylphthalimide are illustrative starting materials for this exchange step and can be obtained from a commercial source.

Step 3—Reduction to Silylamine

The silylalkylimine or silylalkylimide, produced as the second intermediate in the previous step can then be reduced to a corresponding aminoalkylsilane using methods and catalysts conventionally known to those of skill in the art. The reduction is depicted for second intermediate imine compounds in equation (IV), below:

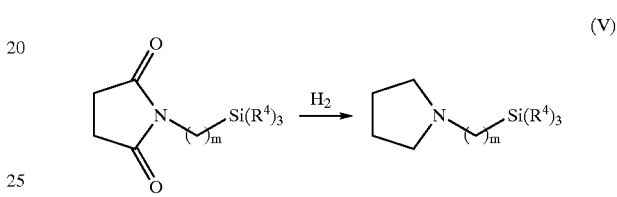

In equation (IV), $R^1$, $R^2$, $R^4$, m and n are as previously defined.

In the case of reduction of an imidoalkylsilane as the second intermediate product, the carbonyl groups of the imidoalkylsilane may be reduced to give a tertiary aminoalkylsilane as illustrated by equation (V):

(V)

In equation (V), $R^4$ and m are as previously defined.

The reduction of this step can be accomplished in a variety of ways. For instance, see *Tetrahedron Letters,* Vol. 39(9), 1998, pages 1017–1020. Catalysts such as palladium on carbon, platinum on carbon, and so forth, have been successfully used.

While many methods have already been reported for the reduction of imines to amines, catalytic hydrogenation is the most economical. The catalysts useful in reducing the second intermediate imine to the corresponding amine include, but are not limited to, nickel, cobalt, platinum, palladium, rhodium, and so forth. Other reducing agents such as aluminum hydrides, borohydrides, hydrosiloxanes, and so forth, are also known and can be employed in this reduction step.

Bis-aminoalkysilane compounds can be produced using the method of the present invention, depending on the starting materials selected. For instance, the use of the difunctional aldehyde terephthaldehyde, results in bis-(aminoalkylsilyl)phenylene compounds.

The secondary and tertiary amino functionalized silanes of the present invention find utility as adhesion promoters and as coupling agents. For instance, the amines can be used as adhesion promoters in adhesives and sealants, and as coupling agents in compositions used in the plastics and glass-fibers industries and in foundries, in fabric treatment compositions, and in personal care products.

In particular, the secondary and tertiary amino functionalized silanes of the present invention are useful as coupling agents in the fiberglass and automotive glass industries.

Alternative Step 2(or Step 1a)—Conversion of Imine to Tertiary Enamine

In some cases it may be desirable to produce a tertiary amine from a ketone or aldehyde starting compound. This can be accomplished if, in the starting aldehyde or ketone, $R^1(CH_2)_nC(=O)R^2$ used in the first step, n is at least 2.

Tertiary amines can be produced from imines by the route of the following equation (VI):

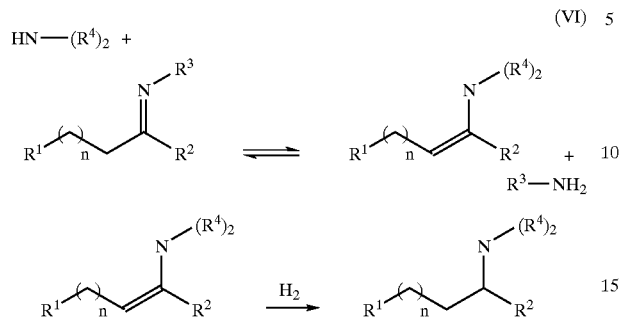

In equation (VI), $R^1$, $R^2$, $R^3$, $R^4$ and n are as defined previously.

The invention is illustrated by the following non-limiting examples.

EXAMPLES

Example 1

N-(phenylmethylene)-3-(trimethoxysilyl)-1-propanamine 25 grams (0.138 moles) of N-benzylidene aniline [cas no. 538-51-2, from TCI America] was combined with 24.7 grams (0.138 moles) of gamma-aminopropyltrimethoxysilane [cas no. 13822-56-5, Silquest A-1110 Silane from Crompton Corporation] and 100 grams of xylene. The resulting slurry was warmed to 90° C. for one hour before a vacuum of 20 mm Hg was applied. Distillation of the xylene and aniline resulted in 36 grams (98%) of N-benzylidene aminopropyltrimethoxysilane [cas no. 67674-55-9] by GC analysis.

Example 2

N-(phenylmethylene)-3-(triethoxysilyl)-1-propanamine 25 grams (0.138 moles) of N-benzylidene aniline [cas no. 538-51-2, from TCI America] was combined with 30.5 grams (0.138 moles) of gamma-aminopropyltriethoxysilane. The resulting solution was warmed to 50° C. for one hours before a vacuum of 20 mm Hg was applied. Heating continued for one hour and vacuum was increased to 2 mm Hg and temperature to 70° C. Stirring continued for an additional three hours. Yield of 36 grams and 98% purity of N-benzylidene aminopropyltriethoxysilane [cas no. 69227-26-5] by GC analysis.

Example 3

N-(phenylmethylene)-3-(triethoxysilyl)-1-propanamine 15 grams (0.1 moles) of N-benzylidene isopropylamine [cas no. 6852-56-8, from Pfaltz and Bauer Co.] was combined with 22.5 grams (0.1 moles) of gamma-aminopropyltriethoxysilane. The resulting solution was warmed to 90° C. and a vacuum of 20 mm Hg was applied. Heating continued for one hour and vacuum was increased to 2 mm Hg. Stirring continued for an additional two hours. Yield of 31 grams and 91% purity of N-benzylidene aminopropyltriethoxysilane [cas no. 69227-26-5] by GC analysis.

Example 4

N-cyclohexylidene-3-(trimethoxysilyl)-1-propanamine 22.5 grams of N-cyclohexylidene-isopropylamine [cas no. 13652-31-8] (see Weingarten, Harold; Chupp, John P.; White, William Andrew J. Org. Chem. 1967, 32(10), 3246–9) was added to 15 g of N-benzylidene isopropylamine and warmed to 90° C. at 200 mm Hg with stirring. After stirring for one hour, vacuum was increased to 1–2 mm Hg and stirring continued an additional three hours. Yield is 98% of N-cyclohexylidene-3-(trimethoxysilyl)-1-propanamine [cas no. 75396-02-0] based on G.C. purity.

Example 5

N,N-(1,4-phenylenedimethylidyne)bis-1-butanamine 16.3 grams (0.121 moles) of terephthalyl dicarboxaldehyde [cas no. 623-27-8, Aldrich Chemical Company] was dissolved in 100 grams of toluene with stirring. To this solution, 18 grams (0.246 moles) of n-butyl amine [cas. No. 109-73-9, Aldrich Chemical Company] was added all at once and allowed to stir at room temperature for two hours. The resulting cloudy white solution was then concentrated under vacuum and at 30° C. to yield 41.8 grams of N,N-(1,4-phenylenedimethylidyne)bis-1-butanamine, CAS no. 30862-11-4.

Example 6

N,N-(1,4-phenylenedimethylidyne)bis[3-(triethoxysilyl)]-1-propanamine 28 grams (0.144 moles) of N,N-(1,4-phenylenedimethylidyne) bis-1-butanamine [cas no. 30862-11-4] was combined with 56 grams (0.253 moles) of gamma-aminopropyltriethoxysilane [cas no. 919-30-2, Silquest A-1100 Silane from Crompton Corporation]. The resulting solution was warmed to 70° C. and a vacuum of 2 mm Hg was applied for two hours to yield 87% of N,N-(1,4-phenylenedimethylidyne)bis[3-(triethoxysilyl)]-1-propanamine [CAS no. 36499-61-3].

While the invention has been described in connection with what is presently considered to be the most practical and preferred embodiments, it is to be understood that the invention is not to be limited to the disclosed embodiments but, on the contrary, is intended to cover various modifications and equivalent arrangements included within the spirit and scope of the appended claims.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. Further, the particular features presented in the dependent claims below can be combined with each other in other manners within the scope of the invention such that the invention should be recognized as also specifically directed to other embodiments having any other possible combination of the features of the dependent claims.

The entire contents of all documents and copending applications mentioned anywhere in the present application are incorporated herein by reference.

What is claimed is:

1. A silylorganoimine of the formula:

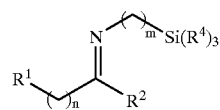

wherein $R^1$ is a hydrocarbon group having from 1 to 30 carbon atoms, $R^2$ is hydrogen or a hydrocarbon group having from 1 to 20 carbon atoms, or $R^1$ and $R^2$ together form a cyclic hydrocarbon group having up to 8 carbon atoms, $R^4$ is hydrogen, a hydrocarbon group having 1 to 8 carbon atoms, or an acyloxy group, m is 2 to 20 and n is 0 to 20.

2. A secondary aminosilane of the formula:

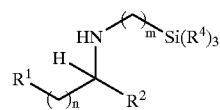

wherein $R^1$ is a hydrocarbon group having from 1 to 30 carbon atoms, $R^2$ is a hydrocarbon group having from 1 to 20 carbon atoms, or $R^1$ and $R^2$ together form a cyclic hydrocarbon group having up to 8 carbon atoms, each $R^4$ is hydrogen, a hydrocarbon group having 1 to 8 carbon atoms, or an acyloxy group, m is 2 to 20 and n is 0 to 20.

3. The silylorganoimine of claim 1 wherein $R^1$ is an aryl, alkaryl, arylalkyl, or alkarylalkyl group.

4. The silylorganoimine of claim 1 wherein $R^1$ is an alkenyl group.

5. The silylorganoimine of claim 1 wherein $R^1$ is an alkynyl group.

6. The silylorganoimine of claim 1 wherein $R^2$ is an aryl, alkaryl, arylalkyl, or alkarylalkyl group.

7. The silylorganoimine of claim 1 wherein $R^4$ is an acyloxy group.

8. The secondary aminosilane of claim 2 wherein $R^1$ is an aryl, alkaryl, arylalkyl, or alkarylalkyl group.

9. The secondary aminosilane of claim 2 wherein $R^1$ is an alkenyl group.

10. The secondary aminosilane of claim 2 wherein $R^1$ is an alkynyl group.

11. The secondary aminosilane of claim 2 wherein $R^2$ is an aryl, alkaryl, arylalkyl, or alkarylalkyl group.

12. The secondary aminosilane of claim 2 wherein $R^4$ is an acyloxy group.

* * * * *